United States Patent [19]

Kanda et al.

[11] Patent Number: 4,597,293

[45] Date of Patent: Jul. 1, 1986

[54] SCANNING ACOUSTIC MICROSCOPE

[75] Inventors: Hiroshi Kanda, Tokorozawa; Isao Ishikawa, Hino; Kageyoshi Katakura, Meguro; Chitose Nakaya, Nishitama, all of Japan

[73] Assignee: Hitachi, Ltd., Tokyo, Japan

[21] Appl. No.: 689,955

[22] Filed: Jan. 9, 1985

[30] Foreign Application Priority Data

Jan. 11, 1984 [JP] Japan .................................. 59-1947

[51] Int. Cl.[4] ............................................. G01N 29/04
[52] U.S. Cl. .................................................... 73/606
[58] Field of Search .......................... 73/606, 644, 627

[56] References Cited
U.S. PATENT DOCUMENTS 4,205,686 6/1980 Harris et al. .......................... 73/644
4,503,708 3/1985 Kino et al. ............................ 73/606

Primary Examiner—Anthony V. Ciarlante
Attorney, Agent, or Firm—Antonelli, Terry & Wands

[57] ABSTRACT

An acoustic microscope wherein an ultrasonic beam is projected on a sample through a propagating medium by an ultrasonic transducer having a short focus, reflected acoustic waves from the sample are detected by the transducer, and a microscopic image of the sample is obtained by scanning the sample mechanically in two dimensions, comprises a cover member which is interposed between the sample and the propagating medium and which has an acoustic impedance higher than those of the two. The intensity of a reflection signal depends upon multipath reflection within the cover member, and an intense reflection signal is obtained even for a sample which differs slightly in the acoustic impedance from the propagating medium.

8 Claims, 7 Drawing Figures

SCANNING ACOUSTIC MICROSCOPE

BACKGROUND OF THE INVENTION

The present invention relates to an acoustic imaging apparatus which exploits high-frequency acoustic energy. More particularly, it relates to an acoustic microscope of the reflection type in which a focused ultrasonic beam is projected on a sample so as to obtain an image on the basis of the resulting reflected acoustic waves.

A scanning acoustic microscope has been proposed and studied as an apparatus for obtaining an image expressive of the microscopic elastic properties of an object to-be-observed by utilizing a hypersonic wave which has an acoustic frequency of 1 GHz and accordingly exhibits an acoustic wavelength of approximately 1.5 μm in the water.

In an example disclosed in U.S. Pat. No. 4,028,933, an acoustic lens whose F number is small is employed for projecting an ultrasonic beam which is very sharply focused on a sample to-be-observed through a propagating medium such as water. On the other hand, while the sample is being scanned mechanically, perturbed energy from the sample is detected, and the detected acoustic waves are displayed on a CRT screen. Thus, microscopic images are obtained.

Setups for detecting the perturbed energy from the sample as described above are classified into two types; the transmission type and the reflection type. In the former, acoustic waves having passed through the sample are detected to obtain an image. Therefore, a transmitting acoustic lens or a transmitting concave transducer and a receiving acoustic lens or a receiving concave transducer are arranged so as to oppose to each other with the sample interposed therebetween. Since the two, transmitting and receiving lenses or concave transducers must be arranged in confocal fashion, adjustments for the alignment thereof become complicated and very subtle. Meanwhile, in the latter, acoustic waves reflected from the sample are detected, so that a single acoustic lens or concave transducer can be used for both the transmission and reception of waves. This brings forth the advantages that the construction of the apparatus is simplified and that the adjustments for the alignment are dispensed with.

A biological tissue which is an important object to be imaged by the acoustic microscope has heretofore been observed with the transmission type apparatus, not with the reflection type apparatus. Concretely, water or a physiological salt solution is used as a propagating medium and is held between the opposing transducers. The sample is supported within this medium in the state in which it is stuck to a film of a thickness and a material that permit the presence thereof to be neglected in propagating the acoustic waves from the medium to the sample.

The reason why such setup of the transmission type has been employed for the observation of the biological tissue, is as follows. The biological tissue is slightly different in the acoustic impedance from the water as the propagating medium, and cannot produce an intense reflection signal. With the reflection type setup, therefore, observation at a high signal-to-noise ratio is impossible.

SUMMARY OF THE INVENTION

An object of the present invention is to provide an acoustic microscope in which even a sample slightly differing in the acoustic impedance from a propagating medium can produce intense reflected acoustic waves, whereby a good image is offered by a reflection type setup.

The characterizing feature of the present invention consists in a construction in which, between a sample and a propagating medium, a cover member greater in the acoustic impedance than the two is interposed.

More concretely, the acoustic microscope of the present invention comprises a transducer unit which transmits an ultrasonic beam converging into a predetermined focus and which detects reflected acoustic waves caused by the transmission, holding means to hold a sample at and near the focus, scanning means to scan relative positions of the sample held by the holding means and the transducer unit, and a propagating liquid medium which fills a gap between the holding medium and the transducer unit, the holding means including a cover member which is interposed between the sample and the propagating medium and which has an acoustic impedance greater than those of the two.

Such construction effectively utilizes multipath reflection within the cover member for image display. Since the intensity of a reflection signal produced through the cover member depends upon the acoustic impedance of the sample located behind the cover member, the distributions of the elastic properties of the sample such as the acoustic impedance can be observed clearly.

DETAILED DESCRIPTION

Now, the present invention will be described in detail with reference to the drawings.

Figure 1:
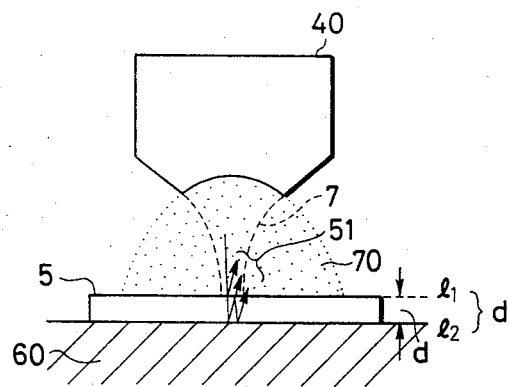
FIG. 1 is a sectional view showing the principle of the present invention.

FIG. 1 is a view for explaining the principle of the present invention, which shows a transducer unit 40 having an acoustic lens, a sample 60, a propagating medium 70 (in case of a biological tissue, water or a physiological salt solution is usually used) filling the interspace between the lens and the sample, and an ultrasonic cover member 5 of thickness d forming the characterizing feature of the present invention. An ultrasonic beam 7 radiated from the lens of the transducer unit 40 is reflected by the upper surface (surface $l_1$) and lower surface (surface $l_2$) of the cover member 5. In this regard, the situation of multipath reflection within the cover member differs depending upon the thickness of the cover member and the acoustic impedance ($Z_L$) and propagating velocity ($v_L$) thereof. By selecting the material and thickness of the cover member, accordingly, it is expected to obtain a reflected acoustic signal which expresses the distributions of the elastic properties of the sample and which has a great reflection factor, accordingly a great magnitude, and to permit imaging at a high signal-to-noise ratio.

Now, let r denote the ratio of the acoustic pressure of reflected ultrasonic waves coming out to the side of the propagating medium 70 as indicated by a plurality of arrows 51 in FIG. 1, relative to the acoustic pressure of the incident acoustic wave, namely, the reflection factor of the system illustrated in FIG. 1. This quantity r is evaluated by the following equation:

$$r = \frac{r_{12} + r_{23} e^{-j\theta}}{1 + r_{12} r_{23} e^{-j\theta}} \quad (1)$$

Here, $$r_{12} = (Z_L - Z_W)/(Z_L + Z_W) \quad (2)$$

$$r_{23} = (Z_S - Z_L)/(Z_S + Z_L) \quad (3)$$

$$\theta = 4\pi d f / v_L \quad (4)$$

where f denotes an ultrasonic frequency used, $Z_L$, $Z_W$ and $Z_S$ denote the acoustic impedances of the cover member 5, propagating medium 70 and sample 60 respectively, and d denotes the thickness of the cover member 5.

From Eq. (1), the absolute value of the acoustic-pressure reflection factor is given by:

$$|r| = \left( \frac{r_{12}^2 + 2r_{12}r_{23}\cos\theta + r_{23}^2}{1 + 2r_{12}r_{23}\cos\theta + r_{12}^2 r_{23}^2} \right)^{\frac{1}{2}} \quad (5)$$

The inventors studied in detail how the acoustic-pressure reflection factor $|r|$ of such system changes depending upon the thickness d (in the above equation, $\theta$) of the cover member 5 and the acoustic impedance $Z_L$ and propagating velocity $v_L$ thereof. Then, it has been found out that in case of interposing between the propagating medium and the sample a cover plate which has an acoustic impedance greater than those of the two and whose thickness is a quarter wavelength, a sufficient reflection factor and accordingly reflected ultrasonic signal are obtained even when the magnitude of the acoustic impedance of the sample changes extending over $0.6-2.0 \times 10^6$ MKS (kg·m$^{-2}$·s$^{-1}$).

Figure 2:
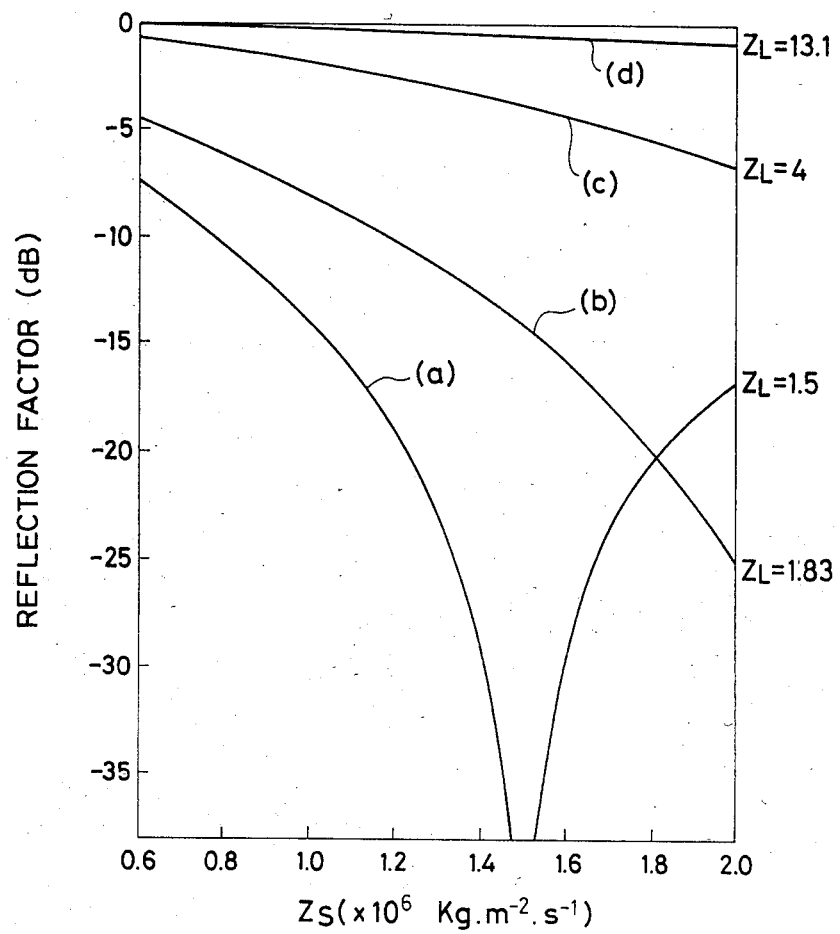
FIG. 2 is a graph showing the characteristics of reflection factors versus the acoustic impedances of samples.

In FIG. 2, the abscissa represents the acoustic impedance $Z_S$ of a sample while the ordinate represents the reflection factor, and the situation of the changes of the reflection factor is illustrated with a parameter being the acoustic impedance $Z_L$ of the quarter-wave plate. The acoustic impedance $Z_W$ of the medium is $1.5 \times 10^6$ MKS. That is, a case of employing water as the propagating medium 70 is assumed.

Curve (a) in the figure illustrates a case of $Z_L = 1.5 \times 10^6$ MKS where the cover member of the present invention has an acoustic impedance equal to that of the medium 70 or is not employed. It is seen that, when the acoustic impedance $Z_S$ of the sample comes close to $1.5 \times 10^6$ MKS, the reflection factor decreases conspicuously. The acoustic impedance $Z_S$ of a biological tissue is distributed near $1.5 \times 10^6$ MKS being the acoustic impedance of water because the content thereof consists mostly of water or a physiological salt solution. Accordingly, reflected ultrasonic waves are not detected in the area of the greater part of the sample.

The circumstances are the most important reason why the transmission method has heretofore been employed for the observation of the biological tissue without using the reflection method. The present invention is intended to eliminate the very difficulty.

Curves (b), (c) and (d) in FIG. 2 are the characteristics of the reflection factor in the cases where the acoustic impedances $Z_L$ of the cover members are $1.83 \times 10^6$ MKS, $4.0 \times 10^6$ MKS and $13.1 \times 10^6$ MKS, respectively. As seen from these curves, the acoustic pressure of the reflected acoustic waves is enhanced more with increase in $Z_L$. A further feature is that the singular point observed at $Z_S = 1.5 \times 10^6$ in the curve (a) in the case of $Z_L = 1.5 \times 10^6$ is not observed in the curves (b), (c) and (d). The singular point arises at $Z_L = Z_S$. When the acoustic impedance $Z_S$ of the sample is distributed above and below the acoustic impedance $Z_L$ of the cover member, the situation occurs in which the reflection intensity and the acoustic impedance of the sample do not correspond in 1-to-1 fashion as in the curve (a) and which is very inconvenient for the interpretation of an image. It is understood that, in order to prevent such situation, the acoustic impedance of the cover plate needs at least to be greater than the acoustic impedance of the sample. Further, in the case of the biological tissue, the acoustic impedance is distributed within a range of approximately $0.6-2.0 \times 10^6$ MKS. When such sample is observed using water as the propagating medium and the cover member of $Z_L = 1.83 \times 10^6$ MKS, the acoustic pressure of reflected acoustic waves is distributed within a range of at least $-25$ dB in comparison with that in the case of total reflection (refer to the curve (b)). Since the acoustic pressure of $-25$ dB can be deemed the lower limit permitting the detection of the reflected waves with the acoustic microscope, it is favorable for such biological tissues that $Z_L$ is $1.83 \times 10^6$ MKS or greater. In the case where $Z_L$ is $4 \times 10^6$ MKS as in the curve (c), the acoustic pressure of reflected waves is more enhanced, and a received signal of high signal-to-noise ratio can be obtained.

Further, in the case of $Z_L = 13.1 \times 10^6$ MKS as in the curve (d), imaging is possible without a singular point in a range of greater acoustic impedances $Z_S$ of the sample, for example, from 0.6 to $10 \times 10^6$ MKS. Regarding biological tissues, staining and identification with heavy metal ions are often performed. The range of the acoustic impedances of such samples can reach $10 \times 10^6$ MKS. The cover member of $Z = 13.1 \times 10^6$ MKS produces favorable results for the observation of such samples.

Figure 3:
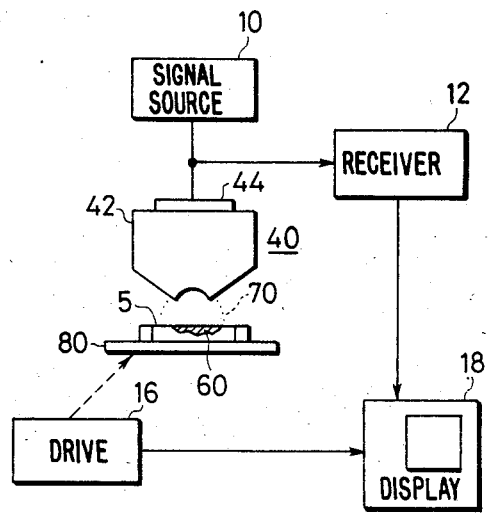
FIG. 3 is a block diagram showing an embodiment of the present invention.
Figure 4:
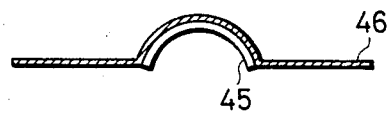
FIG. 4 is a sectional view showing an example of a transducer for use in the embodiment.

FIG. 3 shows the whole arrangement of an embodiment of the present invention. A transducer unit 40 is composed of an acoustic lens 42 which is provided with a concave semispherical hole at one facet thereof, and a piezoelectric element 44 which is mounted on the other facet of the acoustic lens. A signal source 10 and a receiver 12 are connected to the piezoelectric element 44. When an exciting signal in the form of pulses is applied from the signal source 10, an ultrasonic beam converging toward a predetermined focus is transmitted through a propagating medium 70. Near the position of the focus, a sample holder 80 for holding a sample 60 has a cover member 5 installed thereon, and the sample is stuck to the rear side of the cover member 5. Accordingly, the ultrasonic beam enters the sample through the medium 70 as well as the cover member 5. Reflected waves thus produced are detected by the transducer unit 40 through the medium 70, and the detection signal is received by the receiver 12 and is applied to an image display portion 18 as imaging data. Meanwhile, the sample holder 80 is mechanically scanned and driven by a driving portion 16, and the image display portion 18 performs signal processing corresponding to the scanning and displays the image of the sample. The driving portion may drive and scan the relative positions of the focus of the transducer unit and the sample, and may of course drive the transducer unit 40. In addition, the transducer unit 40 may be an ultrasonic transducer having a predetermined focus. Therefore, it may well be the so-called concave transducer, for example, one in which a piezoelectric element 45 is mounted on the semispherical concave surface of a substrate 46 as shown in FIG. 4.

Figure 5:
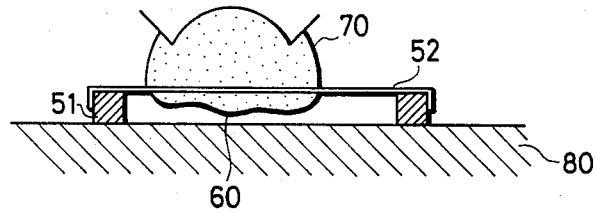
FIG. 5 and FIGS. 6A and 6B are sectional views showing aspects of performance of the present invention.

Examples of the cover plate 5 as described above will be explained below. A polymer sheet can be used as a member close to the example of the acoustic impedance $Z_L = 4 \times 10^6$ MKS mentioned in FIG. 2. The inventors investigated the acoustic characteristics of a polyimide resin which is known as "Vespel" (Trade Mark of Du Pont de Nemours, E. I.). Then, it has been found that the acoustic impedance is $Z_L = 3.5 \times 10^6$ MKS and that the propagating velocity is 2,400 m/s. When this resin was roll-expanded into a sheet 5 $\mu$m thick and the present invention was performed therewith, good results were obtained. In the present example, as shown in FIG. 5, the sheet 52 was stuck to a metal ring 51 having a diameter of 20 mm and a thickness of 5 mm, and a sample 60 was stuck to the rear side thereof. The resultant structure was set on the sample holder 80 of a reflection type acoustic microscope, and the sample was observed. The rear of the sample 60 is surrounded with the air.

As a similar example, the inventors measured the acoustic characteristics of "Stycast 3,050" (Trade Mark of Emerson & Cuming Co.) among epoxy resins, and they have found $Z_L = 3.7 \times 10^6$ MKS and $v_L = 2,400$ m/s. It has been verified that the present invention is realized with a sheet 5 $\mu$m thick. In any case, the thickness of 5 $\mu$m corresponds to a quarter wavelength at an ultrasonic frequency of 120 MHz. The inventors have also found that, even when the thickness of the cover member does not exactly correspond to the quarter wavelength, the purport of the present invention is achieved.

Figure 6A:
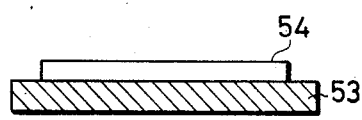
Figure 6B:
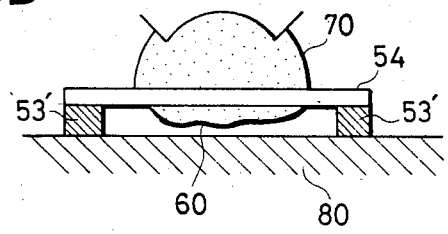

As the example of $Z_L = 13.1 \times 10^6$ MKS in FIG. 2, the inventors used $SiO_2$ and obtained favorable results. More specifically, as shown in FIG. 6A, an $SiO_2$ film 54 was deposited on one surface of a sheet 53 made of steel and having a thickness of 10 $\mu$m, to a thickness of 2 $\mu$m by sputtering. Thereafter, the steel was etched and removed into a hollow state as shown at 53' in FIG. 6B by the use of an acid etc. Then, a structure similar to that of FIG. 5 was fabricated. Since the propagating velocity of $SiO_2$ is $v_L = 6,000$ m/s, this sheet of 2 $\mu$m produced favorable results as a quarter-wave cover member at a frequency of 750 MHz.

As set forth above, according to the present invention, even for a biological tissue whose acoustic characteristics are very close to those of water and which is difficult of imaging with the reflection type, there are attained the effects (1) that equivalently a very great reflection signal is obtained, and a reflected image of high signal-to-noise ratio can be obtained, and (2) that the singular point of a reflection signal which is determined by a medium used is removed, and the distribution of a reflection intensity and the distribution of an acoustic impedance within the surface of a sample correspond in 1-to-1 fashion, so a clear image display is possible. Incidentally, since the cover member functions as a protective film for the sample, there is the effect that the invention is convenient for samples, such as swelling samples, which are improper for direct contact with water or a salt solution as the medium.

We claim:

1. In an acoustic microscope having a transducer unit which transmits an ultrasonic beam toward a predetermined focus and which detects reflected acoustic waves caused by the transmission, holding means to hold a sample at and near the focus, and a propagating liquid medium which is held between the sample and the transducer unit, the acoustic impedance of the sample being distributed in a range near the acoustic impedance of the propagating medium, the reflected acoustic waves from the sample being detected and being used as image data for an image distribution of the acoustic impedance of the sample, the improvement comprising a cover member which has an acoustic impedance greater than the acoustic impedance of said propagating medium and said sample is interposed between said propagating medium and said sample.

2. An acoustic microscope according to claim 1, wherein a thickness of said cover member is substantially a quarter wavelength of an ultrasonic wave used.

3. An acoustic microscope comprising:
a transducer unit which transmits an ultrasonic beam converging into a predetermined focus and which detects reflected acoustic waves caused by the transmission,
holding means to hold a sample at and near the focus,
scanning means to mechanically scan relative positions of the sample held by said holding means and said transducer unit, and
a propagating liquid medium which fills a gap between said holding means and said transducer unit,
said holding means including a cover member which is interposed between said sample and said propagating medium and which has an acoustic impedance greater than the acoustic impedance of said sample and said propagating medium.

4. An acoustic microscope according to claim 3, wherein a thickness of said cover member is substantially a quarter wavelength of an ultrasonic wave used.

5. An acoustic microscope according to claim 3, wherein said cover member is a polymer sheet stuck to a ring-shaped member.

6. An acoustic microscope according to claim 3, wherein said cover member is an inorganic film.

7. An acoustic microscope according to claim 6, wherein said cover member is an $SiO_2$ film.

8. An acoustic microscope according to claim 3, wherein said propagating medium is water, and the acoustic impedance of said cover member is at least $1.83 \times 10^6$ MKS.

* * * * *